United States Patent [19]

Brandes et al.

[11] Patent Number: 4,568,672

[45] Date of Patent: Feb. 4, 1986

[54] 3,6-DISUBSTITUTED 2-THIOXO-1,3,5-THIADIAZIN-4-ONES

[75] Inventors: Wilhelm Brandes; Rolf Bunnenberg, both of Leichlingen; Gerd Hänssler; Paul Reinecke, both of Leverkusen; Karlfried Wedemeyer, Cologne, all of Fed. Rep. of Germany

[73] Assignee: Bayer Aktiengesellschaft, Leverkusen, Fed. Rep. of Germany

[21] Appl. No.: 644,732

[22] Filed: Aug. 27, 1984

[30] Foreign Application Priority Data

Sep. 17, 1983 [DE] Fed. Rep. of Germany ....... 3333659

[51] Int. Cl.[4] .................. C07D 285/34; C07D 417/12; A01N 43/88
[52] U.S. Cl. ......................................... 514/222; 544/8
[58] Field of Search ............................ 424/246; 544/8; 514/222

[56] References Cited

FOREIGN PATENT DOCUMENTS 3010238 9/1981 Fed. Rep. of Germany .
2358401 2/1978 France .

OTHER PUBLICATIONS

Chemie der Pflanzenschutz–und Schädlingsbekämpfungsmittel, vol. 2, pp. 126–127, Springer Verlag, Berlin-Heidelberg-New York, 1970.

*Primary Examiner*—John M. Ford

[57] ABSTRACT

3,6-Disubstituted 2-thioxo-1,3,5-thiadiazin-4-ones of the formula

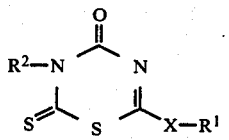

in which
$R^1$ represents hydrogen; alkyl which is optionally monosubstituted or polysubstituted by identical or different substituents; alkenyl which is optionally monosubstituted or polysubstituted by identical or different substituents; alkinyl which is optionally monosubstituted or polysubstituted; cycloalkenyl or cycloalkyl which is optionally monosubstituted or polysubstituted by identical or different substituents; aryl or aralkyl which is optionally monosubstituted or polysubstituted by identical or different substituents; or a heterocyclic structure which is monosubstituted or polysubstituted by identical or different substituents;
$R^2$ represents alkenyl or alkyl which is optionally monosubstituted or polysubstituted by identical or different substituents; cycloalkenyl or cycloalkyl which is optionally monosubstituted or polysubstituted by identical or different substituents; aralkyl which is optionally monosubstituted or polysubstituted by identical or different substituents; or the fluorenyl radical; and X represents oxygen or sulphur.

which possess fungicidal activity.

10 Claims, No Drawings

3,6-DISUBSTITUTED 2-THIOXO-1,3,5-THIADIAZIN-4-ONES

The present invention relates to new 3,6-disubstituted 2-thioxo-1,3,5-thiadiazin-4-ones, a process for their preparation and their use as pest-combating agents.

It has been disclosed that monosubstituted 1,3,5-thiadiazines, such as, for example, 2,3-dihydro-6-methoxy-2-thioxo-4H-1,3,5-thiadiazin-4-one, possess good fungicidal properties (see DE-OS (German Published Specification) 3,101,238).

Furthermore, disubstituted and trisubstituted thioxo-1,3,5-thiadiazine compounds are known, such as, for example, 3,5-dimethyltetrahydro-1,3,5-thiadiazine-2-thione, 3-methyl-5-carboxymethyl-tetrahydro-1,3,5-thiadiazine-2-thione and 3,3'-ethylene-bis-[tetrahydro-4,6-dimethyl-1,3,5-thiadiazine-2-thione]. These compounds, too, have fungicidal properties (see, for example, R. Wegler, "Chemie der Pflanzenschutz- und Schädlingsbekämpfungsmittel" (Chemistry of plant protection agents and pest-combating agents), Vol. 2, pages 126–127, Springer Verlag Berlin-Heidelberg-New York 1970).

In the case of all of these compounds, the action is not always completely satisfactory under certain conditions, for example when low concentrations are used.

New 3,6-disubstituted 2-thioxo-1,3,5-thiadiazin-4-ones of the general formula (I)

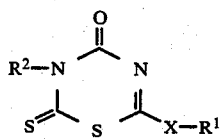

in which
R$^1$ represents hydrogen; alkyl which is optionally monosubstituted or polysubstituted by identical or different substituents; alkenyl which is optionally monosubstituted or polysubstituted by identical or different substituents; alkinyl which is optionally monosubstituted or polysubstituted; cycloalkenyl or cycloalkyl which is optionally monosubstituted or polysubstituted by identical or different substituents; aryl or aralkyl which is optionally monosubstituted or polysubstituted by identical or different substituents; or a heterocyclic structure which is monosubstituted or polysubstituted by identical or different substituents;
R$^2$ represents alkenyl or alkyl which is optionally monosubstituted or polysubstituted by identical or different substituents; cycloalkenyl or cycloalkyl which is optionally monosubstituted or polysubstituted by identical or different substituents; aralkyl which is monosubstituted or polysubstituted by identical or different substituents; or the fluorenyl radical; and
X represents oxygen or sulphur,
have been found.

Furthermore, it has been found that the 3,6-disubstituted 2-thioxo-1,3,5-thiadiazin-4-ones of the formula (I)

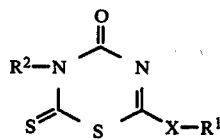

in which
R$^1$ represents hydrogen; alkyl which is optionally monosubstituted or polysubstituted by identical or different substituents; alkenyl which is optionally monosubstituted or polysubstituted by identical or different substituents; alkinyl which is optionally monosubstituted or polysubstituted; cycloalkenyl or cycloalkyl which is optionally monosubstituted or polysubstituted by identical or different substituents; aryl or aralkyl which is optionally monosubstituted or polysubstituted by identical or different substituents; or a heterocyclic structure which is monosubstituted or polysubstituted by identical or different substituents;
R$^2$ represents alkenyl or alkyl which is optionally monosubstituted or polysubstituted by identical or different substituents; cycloalkenyl or cycloalkyl which is optionally monosubstituted or polysubstituted by identical or different substituents; aralkyl which is monosubstituted or polysubstituted by identical or different substituents; or the fluorenyl radical; and
X represents oxygen or sulphur,
are obtained if 1,3,5-thiadiazines of the formula (II)

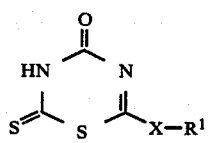

in which R$^1$ and X have the meaning given above, are reacted with diazo compounds of the formula (III)

in which R$^{2'}$ represents alkenylene, cycloalkylene, cycloalkenylene, aralkylene or alkylene which is optionally monosubstituted or polysubstituted by identical or different substituents, or represents the fluorenylene radical,
if appropriate in the presence of an inert diluent.

The new 3,6-disubstituted 2-thioxo-1,3,5-thiadiazin-4-ones of the formula (I) possess powerful biological properties, especially fungicial properties. In this respect, the compounds according to the invention surprisingly show a better fungicidal action than the fungicidal active compounds known from the prior art.

The new compounds thus represent an enrichment of the art.

Formula (I) gives a general definition of the 3,6-disubstituted 2-thioxo-1,3,5-thiadiazin-4-ones according to the invention. Preferred compounds of the formula (I) are those in which
R$^1$ represents hydrogen; alkyl which is monosubstituted to pentasubstituted by identical or different substituents and has 1 to 12 carbon atoms, such as, for example, methyl, ethyl, propyl, isopropyl, butyl, isobutyl, tert.-butyl, pentyl, hexyl, isohexyl, octyl, isooctyl, decyl, isodecyl, dodecyl or isododecyl, substituents which may be mentioned being nitro, cyano, isocyanato, halogen, hydroxyl, alkoxy having 1 to 4 carbon atoms, mercapto, alkylthio having 1 to 4 carbon atoms, alkylcarbonyl having 1 to 5 carbon atoms in the alkyl part, alkylcarbonyloxy having 1 to 5 carbon atoms and alkoxycarbonyl having 1 to 5 carbon atoms in the alkoxy part; alkenyl which is optionally monosubstituted to pentasubstituted by identical or different substituents and has 2 to 12 carbon atoms, such as, for example, allyl, butenyl, isobutenyl, hexenyl, isohexenyl, octenyl, isooctenyl, decenyl, isodecenyl, dodecenyl and isododecenyl, substituents which may be mentioned being halogen, cyano, alkoxy having 1 to 4 carbon atoms, alkylthio having 1 to 4 carbon atoms, alkylcarbonyl and alkylcarbonyloxy, each having 1 to 5 carbon atoms in the alkyl part, and alkoxycarbonyl having 1 to 5 carbon atoms; alkinyl which is optionally monosubstituted or pentasubstituted and has 3 to 12 carbon atoms, such as, for example, propargyl, butinyl, pentinyl, hexinyl, isohexinyl, heptinyl, octinyl and dodecinyl, substituents which may be mentioned being halogen, alkoxy and alkylthio having 1 to 4 carbon atoms per alkyl part, alkylcarbonyl and alkylcarbonyloxy, each having 1 to 5 carbon atoms per alkyl part, and alkoxycarbonyl having 1 to 5 carbon atoms; cycloalkyl which is optionally monosubstituted to pentasubstituted by identical or different substituents and has 3 to 9 carbon atoms, such as, for example, cyclopropyl, cyclobutyl, cyclopentyl, cyclohexyl, cycloheptyl or cyclooctyl, substituents which may be mentioned being halogen, alkoxy and alkylthio, each having 1 to 4 carbon atoms, alkyl, alkylcarbonyl and alkylcarbonyloxy, each having 1 to 5 carbon atoms per alkyl part, alkoxycarbonyl having 1 to 5 carbon atoms in the alkoxy part, and halogenoalkyl having 1 to 3 carbon atoms and 1 to 5 identical or different halogen atoms; cycloalkenyl which is optionally monosubstituted to pentasubstituted by identical or different substituents and has 3 to 8 carbon atoms, such as, for example, cyclopentenyl, cyclohexenyl, cycloheptenyl or cyclooctenyl, substituents which may be mentioned being halogen, alkyl and alkoxy, each having 1 to 4 carbon atoms, and halogenoalkyl having 1 to 3 carbon atoms and 1 to 5 identical or different halogen atoms; aryl which is optionally monosubstituted to pentasubstituted by identical or different substituents and has 6 to 14 carbon atoms or aralkyl which has 1 to 3 carbon atoms in the alkyl part and 6 to 14 carbon atoms in the aryl part, such as, for example, phenyl, naphthyl, anthryl or benzyl, α-phenylethyl, β-phenylethyl, napthylmethyl, naphthylethyl, anthrylmethyl and anthrylethyl, and as substituents in the aryl part halogen, phenyl, nitro, cyano, isocyanato, hydroxyl, mercapto, alkyl having 1 to 4 carbon atoms, alkoxy and alkoxycarbonyl, each having 1 to 5 carbon atoms per alkoxy part, alkylcarbonyl and alkylcarbonyloxy, each having 1 to 5 carbon atoms per alkyl part, alkylthio having 1 to 5 carbon atoms, halogenoalkyl, halogenoalkoxy and halogenoalkylthio having 1 to 3 carbon atoms and 1 to 5 identical or different halogen atoms per halogenoalkyl radical; a 5-membered or 6-membered heterocyclic structure which is optionally monosubstituted or pentasubstituted by identical or different substituents and has 1 to 3 identical or different heteroatoms, such as oxygen, sulphur or nitrogen, substituents which may be mentioned being halogen, alkyl having 1 to 4 carbon atoms, halogenoalkyl and halogenoalkoxy having 1 to 3 carbon atoms and 1 to 5 identical or different halogen atoms, or alkoxy having 1 to 6 carbon atoms, or 2 substituents on a carbon atom together can form an alkylene radical having 4 or 5 carbon atoms;

$R^2$ represents alkyl or alkenyl which is monosubstituted to pentasubstituted by identical or different substituents and has up to 12 carbon atoms, as stated under $R^1$, halogen, nitro, cyano or alkoxy having 1 to 5 carbon atoms being mentioned as substituents; cycloalkyl or cycloalkenyl, each of which is monosubstituted to pentasubstituted by identical or different substituents and has 3 to 8 carbon atoms, as stated under $R^1$, halogen, alkyl and alkoxy, each having 1 to 4 carbon atoms, and halogenoalkyl having 1 to 3 carbon atoms and 1 to 5 identical or different halogen atoms being mentioned as substituents; or a fluorenyl radical which is optionally monosubstituted to pentasubstituted by identical or different substituents or aralkyl which has 6 to 14 carbon atoms in the aryl part and 1 to 3 carbon atoms in the alkyl part, such as, for example, benzyl, substituents in the aryl part which may be mentioned being phenyl, halogen, nitro, cyano, or alkyl or alkoxy, each having 1 to 5 carbon atoms; and X represents oxygen or sulphur.

Very particularly preferred compounds of the formula (I) are those in which $R^1$ represents hydrogen; straight-chain or branched alkyl having 1 to 12 carbon atoms; alkenyl having 2 to 6 carbon atoms; alkyl which has 1 to 4 carbon atoms and is monosubstituted by nitro, cyano, isocyanato, fluorine, chlorine, bromine, iodine, hydroxyl, alkoxy having 1 to 3 carbon atoms, such as methoxy, ethoxy, n- and iso-propoxy, mercapto, alkylthio having 1 to 3 carbon atoms, such as methylthio, ethylthio, n- and iso-propylthio, alkylcarbonyl and alkylcarbonyloxy having 1 to 3 carbon atoms in the alkyl part, such as methylcarbonyl, methylcarbonyloxy, ethylcarbonyl, ethylcarbonyloxy, n- and iso-propylcarbonyl and n- and iso-propylcarbonyloxy, and alkoxycarbonyl having 1 to 3 carbon atoms in the alkoxy part, such as methoxycarbonyl, ethoxycarbonyl and n- and iso-propoxycarbonyl; and alkenyl having 2 to 6 carbon atoms; alkinyl which has 3 or 4 carbon atoms in the alkinyl part and is monosubstituted by fluorine, chlorine, bromine, iodine, alkoxy or alkylthio, each having 1 to 3 carbon atoms, such as methoxy, ethoxy, n- and iso-propoxy, methylthio, ethylthio, n- and iso-propylthio, alkylcarbonyl and alkylcarbonyloxy, each having 1 to 3 carbon atoms per alkyl part, such as methylcarbonyl, ethylcarbonyl, propylcarbonyl, methylcarbonyloxy, ethylcarbonyloxy and propylcarbonyloxy; cyclohexyl, cyclopentenyl, cyclohexenyl, cycloheptenyl and cyclopentyl which is optionally monosubstituted to trisubstituted by methyl or ethyl; naphthyl, benzyl, phenylethyl, naphthylethyl, naphthylmethyl and phenyl which is optionally monosubstituted to trisubstituted by identical or different substituents from amongst fluorine, chlorine, nitro, cyano, bromine, iodine, isocyanato, phenyl, methyl, ethyl n- and iso-propyl, tert.-butyl, mercapto, methoxy, ethoxy, propoxy, methoxycarbonyl, ethoxycarbonyl, methylcarbonyl, ethylcarbonyl, propylcarbonyl, trichloromethyl, fluorodichloromethyl, trichloroethyl, trichloromethoxy and trichloroethoxy; and furyl, pyrrolyl, imidazolyl, pyrazinyl, isoxazolyl, morpholinyl, 1,5-dioxaspiroundecanyl and 1,3-dioxa-cyclohexyl which is optionally monosubstituted to trisubstituted by fluorine, chlorine, methyl, ethyl or propyl;

$R^2$ represents alkyl having 1 to 5 carbon atoms; alkyl and alkenyl, each of which has up to 6 carbon atoms per radical and is monosubstituted by fluorine, chlorine, bromine, cyano or alkoxy having 1 to 3 carbon atoms, such as methoxy, ethoxy and propoxy; cycloalkyl and cycloalkenyl, each of which has 4 to 7 carbon atoms and is optionally substituted by alkyl having 1 to 3 carbon atoms, such as methyl, ethyl and propyl; and fluorenyl and benzyl which is optionally monosubstituted to trisubstituted in the aryl part by phenyl, fluorine, chlorine, bromine, nitro and alkyl and alkoxy, each having 1 to 3 carbon atoms, such as methyl, ethyl, propyl, methoxy, ethoxy and propoxy; and X represents oxygen or sulphur.

If, for example, 2,3-dihydro-6-phenylthio-2-thioxo-4H-1,3,5-thiadiazin-4-one and diazomethane are used, the course of the reaction can be represented by the following equation:

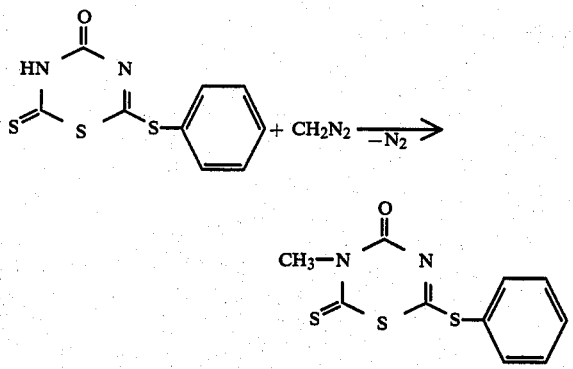

Formula (II) gives a general definition of the 2-thioxo-1,3,5-thiadiazin-4-ones to be used as starting materials in carrying out the process according to the invention. In this formula, $R^1$ and X preferably represent those radicals which have already been mentioned in connection with the description of the substances according to the invention, of the formula (I), as being preferred for these substituents.

Some of the 1,3,5-thiadiazines of the formula (II) are known (see DE-OS (German Published Specification) 3,010,204, DE-OS (German Published Specification) 2,010,237 and DE-OS (German Published Specification) 3,010,238).

Both the new and the known compounds can be obtained by the process stated therein, by reacting carbonyl diisothiocyanate of the formula (IV)

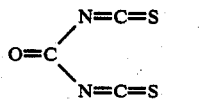 (IV)

with compounds of the formula (V)

$$R^1-X-H \qquad (V)$$

in which $R^1$ and X have the meaning given above, in the presence of an inert solvent, such as, for example, ethers, esters, hydrocarbons or halogenated hydrocarbons.

The majority of the diazo compounds of the formula (III) which are furthermore required as starting materials are known or can be obtained in a generally known manner (see Houben-Weyl Vol. X/4).

Suitable diluents for the reaction according to the invention are inert organic solvents. These preferably include ethers, such as, for example, diethyl ether, dimethoxyethane, tetrahydrofuran and dioxane; hydrocarbons, such as, for example, hexane, ligroin fractions, benzene, toluene and xylene; and halogenated hydrocarbons, such as, for example, methylene chloride, chloroform, carbon tetrachloride, chlorobenzene or dichlorobenzene. One of the stated ethers is particularly preferably used.

The reaction temperatures can be varied within a substantial range. In general, the reaction is carried out at between $-10°$ C. and $+60°$ C., preferably at 0° C. to 30° C.

In carrying out the process according to the invention, preferably 1 to 1.5 mols of the compound of the formula (III) are employed per mol of the compound of the formula (II). To isolate the compounds of the formula (I), the solvent is distilled off and the residue is purified by recrystallisation or extraction. In a variant of the process according to the invention, the 1,3,5-thiadiazine of the formula (II) which is formed by reaction of the carbonyl diisocyanate of the formula (IV) with compounds of the formula (V) is not isolated at an intermediate stage, but is reacted directly with a compound of the formula (III) to give 3,6-disubstituted 2-thioxo-1,3,5-thiadiazin-4-ones of the general formula (I).

The active compounds according to the invention exhibit a powerful microbicidal action and can be employed in practice for combating undesired microorganisms. The active compounds are suitable for use as plant protection agents.

Thus, for example, fungicidal agents can be employed in plant protection for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

In plant protection, the compounds according to the invention can be employed with particularly good success for combating Puccinia, Leptosphaeria and Venturia species, against fungal pathogens on rice, such as, for example, Pyricularia. In addition, they have, for example, a good fungicidal action against powdery mildew, Cochliobolus sativus and Pyrenophora teres on cereals. When used in an appropriate manner, they also exhibit insecticidal and acaricidal activity.

The active compounds can be converted to the customary formulations, such as solutions, emulsions, suspensions, powders, foams, pastes, granules, aerosols, very fine capsules in polymeric substances and in coating compositions for seed, and ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Further additives can be mineral or vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, bird repellents, growth factors, plant nutrients and agents for improving soil structure.

The active compounds can be used as such or in the form of their formulations or the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, painting on, etc. It is also possible to apply the active compounds by the ultra-low volume method, or to inject the preparation of active compound, or the active compound itself, into the soil. It is also possible to treat the seed of the plants.

In the treatment of parts of plants, the active compound concentrations in the use forms can be varied within a substantial range. They are, in general, between 1 to 0.0001% by weight, preferably between 0.5 and 0.001%.

In the treatment of seed, amounts of active compound of 0.001 and 50 g per kilogram of seed, preferably 0.01 to 10 g, are generally required.

For the treatment of the soil, active compound concentrations of 0.00001 to 0.1% by weight, preferably 0.0001 to 0.02%, are required at the place of action.

The preparation examples which follow are intended to illustrate the process according to the invention.

PREPARATION EXAMPLES

Example 1

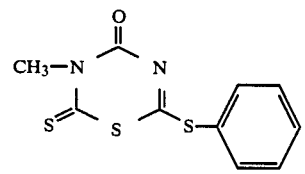

A solution of diazomethane in ether is added in portions to a solution of 10.2 g of 2,3-dihydro-6-phenylthio-2-thioxo-4H-1,3,5-thiadiazin-4-one in 200 ml of tetrahydrofuran at 22° C., until evolution of nitrogen is no longer observed. Excess diazomethane is destroyed by adding acetic acid, the solvent is distilled off, 20 ml of ether are added to the residue, and the precipitate is filtered off under suction.

6.2 g of 3-methyl-6-phenylthio-2-thioxo-1,3,5-thiadiazin-4-one are obtained in the form of yellow crystals of melting point 116°–118° C. Molecular weight 268 (MS).

IR (KBr): $C=O = 1722$ cm$^{-1}$, $C=N$ 1548, $C=S$ 1228

$^1$H-NMR (CDCl$_3$): CH$_3$ = 3.8 ppm (s), CH$_{arom.}$ 7.6 (m)

C$_{10}$H$_8$N$_2$OS$_3$ (268.4): calculated C=44.8 H=3.0 N=10.4 S=35.8; found C=44.3 H=3.0 N=10.4 S=36.2

Example 2

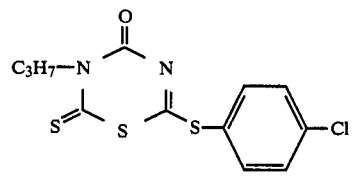

A solution of 7.7 g of diazopropane in ether is added in portions to a solution of 28.8 g of 2,3-dihydro-6-(4-chlorophenylthio)-2-thioxo-4H-1,3,5-thiadiazin-4-one in 250 ml of tetrahydrofuran at 22° C. The solvent is distilled off, the residue is taken up in a small amount of methanol, and the precipitate is filtered off under suction, washed with methanol and dried. 21.9 g of 3-propyl-6-(4-chlorophenylthio)-2-thioxo-1,3,5-thiadiazin-4-one are obtained in the form of yellow crystals of melting point 151°–152° C.

PREPARATION OF THE STARTING MATERIAL

A solution of 14.4 g of p-chlorothiophenol in 150 ml of tetrahydrofuran is added dropwise to a solution of 14.4 g of carbonyl diisothiocyanate in 150 ml of tetrahydrofuran at 0°–5° C. The mixture is stirred for 3 hours and is allowed to warm up to 22° C. during this procedure. By adding benzine, 13.8 g of yellow crystals of melting point 172°–174° C. (decomposition) are precipitated.

The examples below, of the general formula (I)

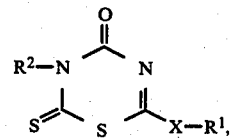

are obtained in a manner corresponding to Examples 1 and 2:

| Example No. | $R^1$ | X | $R^2$ | Melting point (°C.) |
|---|---|---|---|---|
| 3 | $-C_2H_5$ | O | $CH_3$ | 88–89 |
| 4 | $-C_2H_5$ | S | $CH_3$ | 75–76 |
| 5 | $-CH(CH_3)COOC_2H_5$ | O | $CH_3$ | 75–76 |
| 6 | $-CH_2-CH_2-O-CH_3$ | O | $CH_3$ | 61–62 |
| 7 | $-CH_2-\text{C}_6\text{H}_5$ | O | $CH_3$ | 87–88 |
| 8 | (spiro dioxolane cyclohexyl group) | O | $CH_3$ | Resin |
| 9 | $-C_{12}H_{25}$ | O | $CH_3$ | 57–58 |
| 10 | $-C_8H_{17}$ | O | $CH_3$ | 54–55 |
| 11 | $-CH_2-\text{C}_6\text{H}_5$ | S | $CH_3$ | 59–61 |
| 12 | $-\text{C}_6\text{H}_4\text{-Cl}$ | S | $CH_3$ | 164–165 |
| 13 | $-C(CH_3)_3$ | S | $CH_3$ | 109–110 |
| 14 | $-CH_2-CH_2-OH$ | S | $CH_3$ | 135–136 |
| 15 | $-\text{C}_6\text{H}_5$ | S | $C_2H_5$ | 97–100 |
| 16 | $-CH_2-CH=CH_2$ | O | $CH_3$ | 45–46 |
| 17 | $-CH_3$ | S | $CH_3$ | 98–100 |
| 18 | $-C_{12}H_{25}$ | S | $CH_3$ | 55–56 |
| 19 | $-\text{C}_6\text{H}_4\text{-CH}_3$ | S | $CH_3$ | 120–122 |
| 20 | $-\text{C}_6\text{H}_2\text{Cl}_3$ (2,4,5-trichlorophenyl) | S | $CH_3$ | 174–176 |

-continued

| Example No. | R¹ | X | R² | Melting point (°C.) |
|---|---|---|---|---|
| 21 | 3,4-dichlorophenyl | S | $CH_3$ | 180–183 |
| 22 | 4-tert-butylphenyl | S | $CH_3$ | 121–122 |
| 23 | $-CH_2-CH=CH_2$ | O | $C_2H_5$ | oil |
| 24 | $-CH(CH_3)_2$ | O | $CH_3$ | 58–59 |
| 25 | $-CH_3$ | O | $CH_3$ | 91–92 |
| 26 | $-CH_2-C(=O)-OCH_3$ | S | $CH_3$ | 66–67 |
| 27 | pentachlorophenyl | S | $CH_3$ | 198–201 |
| 28 | 2,6-dichlorophenyl | S | $C_2H_5$ | 189–190 |
| 29 | 2,5-dichlorophenyl | S | $CH_3$ | 149–150 |
| 30 | 4-methylphenyl | S | $n-C_3H_7$ | 117–119 |
| 31 | 3,4,5-trichlorophenyl | S | $n-C_3H_7$ | 145–149 |
| 32 | 4-chlorophenyl | S | $CH_3-O-CH_2-CH_2-$ | 116–118 |
| 33 | 4-chlorophenyl | S | $C_2H_5$ | 157–160 |

-continued

| Example No. | R¹ | X | R² | Melting point (°C.) |
|---|---|---|---|---|
| 34 | ⟨C₆H₄⟩—NO₂ | S | C₂H₅ | 161–163 |
| 35 | ⟨C₆H₄⟩—Cl | S | CH₃ | 165–167 |
| 36 | ⟨C₆H₄⟩—Cl | S | C₆H₅—CH₂— | Resin |
| 37 | ⟨C₆H₄⟩—OCH₃ | S | CH₃ | 140–141 |
| 38 | —CH₂—C≡CO | O | CH₃ | 139–140 |

USE EXAMPLES

In the use examples which follow, the compound listed below is employed as a comparative substance:

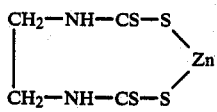

Zinc ethylenebisdithiocarbamate

Example A

Puccinia test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: 1 and 5.

Example B

Leptosphaeria nodorum test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compound according to preparation Example 1.

Example C

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 1, 5 and 7.

Example D

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compound according to preparation Example 1.

Example E

Pyricularia test (rice)/systemic

Solvent: 12.5 parts by weight of acetone
Emulsifier: 0.3 parts by weight of alkylaryl polyglycol ether To produce a suitable preparation of active compound, 1 parts by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 1 and 9.

It is understood that the specficiation and examples are illustrative but not limitative of the present invention and that other embodiments within the spirit and scope of the invention will suggest themselves to those skilled in the art.

We claim:

1. A 3,6-disubstituted 2-thioxo-1,3,5-thiadiazin-4-one of the formula

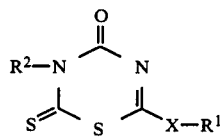

in which
$R^1$ represents hydrogen; alkyl which is monosubstituted to pentasubstituted by identical or different substituents and has 1 to 12 carbon atoms, the substituents being nitro, cyano, isocyanato, halogen, hydroxyl, alkoxy having 1 to 4 carbon atoms, mercapto, alkylthio having 1 to 4 carbon atoms, alkylcarbonyl having 1 to 5 carbon atoms in the alkyl part, alkylcarbonyloxy having 1 to 5 carbon atoms and alkoxycarbonyl having 1 to 5 carbon atoms in the alkoxy part; alkenyl which is optionally monosubstituted to pentasubstituted by identical or different substituents and has 2 to 12 carbon atoms, the substituents being halogen, cyano, alkoxy having 1 to 4 carbon atoms, alkylthio having 1 to 4 carbon atoms, alkylcarbonyl and alkylcarbonyloxy, each having 1 to 5 carbon atoms in the alkyl part, and alkoxycarbonyl having 1 to 5 carbon atoms; alkinyl which is optionally monosubstituted to pentasubstituted and has 3 to 12 carbon atoms, the substituents being halogen, alkoxy and alkylthio having 1 to 4 carbon atoms per alkyl part, alkylcarbonyl and alkylcarbonyloxy having 1 to 5 carbon atoms per alkyl part, and alkoxycarbonyl having 1 to 5 carbon atoms; cycloalkyl which is optionally monosubstituted to pentasubstituted by identical or different substituents and has 3 to 9 carbon atoms, the substituents being halogen, alkoxy, and alkylthio, each having 1 to 4 carbon atoms, alkyl, alkylcarbonyl and alkylcarbonyloxy having 1 to 5 carbon atoms per alkyl part, alkoxycarbonyl having 1 to 5 carbon atoms per alkoxy part, and halogenoalkyl having 1 to 3 carbon atoms and 1 to 5 identical or different halogen atoms; cycloalkenyl which is optionally monosubstituted to pentasubstituted by identical or different substituents and has 3 to 8 carbon atoms, the substituents being halogen, alkyl and alkoxy, each having 1 to 4 carbon atoms, and halogenoalkyl having 1 to 3 carbon atoms and 1 to 5 identical or different halogen atoms; aryl which is optionally monosubstituted to pentasubstituted by identical or different substituents and has 6 to 14 carbon atoms or aralkyl which has 1 to 3 carbon atoms in the alkyl part and 6 to 14 carbon atoms in the aryl part, the substituents in the aryl part being halogen, phenyl, nitro, cyano, isocyanato, hydroxyl, mercapto, alkyl having 1 to 4 carbon atoms, alkoxy and alkoxycarbonyl having 1 to 5 carbon atoms per alkoxy part, alkylcarbonyl and alkylcarbonyloxy, each having 1 to 5 carbon atoms per alkyl part, alkylthio having 1 to 5 carbon atoms, halogenoalkyl, halogenoalkoxy and halogenoalkylthio having 1 to 3 carbon atoms and 1 to 5 identical or different halogen atoms per halogenoalkyl radical; furyl, pyrrolyl, imidazolyl, pyrazinyl, isoxazolyl, morpholinyl, 1,5-dioxaspiroundecanyl and 1,3-dioxa-cyclohexyl which is optionally monosubstituted to pentasubstituted by identical or different substituents and has 1 to 3 oxygen, sulphur and/or nitrogen atoms, the substituents being halogen, alkyl having 1 to 4 carbon atoms, halogenoalkyl and halogenoalkoxy having 1 to 3 carbon atoms and 1 to 5 identical or different halogen atoms, or alkoxy having 1 to 6 carbon atoms, or 2 substituents on a carbon atom together represent an alkylene radical having 4 or 5 carbon atoms; and $R^1$ represents alkyl or alkenyl which is monosubstituted to pentasubstituted by identical or different substituents and has up to 12 carbon atoms, the substituents being halogen, nitro, cyano or alkoxy having 1 to 5 carbon atoms; cycloalkyl or cycloalkenyl, each of which is monosubstituted to pentasubstituted by identical or different substituents and has 3 to 8 carbon atoms, the substituents being halogen, alkyl and alkoxy, each having 1 to 4 carbon atoms, and halogenoalkyl having 1 to 3 carbon atoms and 1 to 5 identical or different halogen atoms; or fluorenyl which is optionally monosubstituted to pentasubstituted by identical or different substituents or aralkyl which has 6 to 14 carbon atoms in the aryl part and 1 to 3 carbon atoms in the alkyl part, substituents in the aryl part being phenyl, halogen, nitro, cyano, or alkyl or alkoxy, each having 1 to 5 carbon atoms.

2. A compound according to claim 1, in which $R^1$ represents hydrogen; straight-chain or branched alkyl having 1 to 12 carbon atoms; alkenyl having 2 to 6 carbon atoms; alkenyl having 2 to 6 carbon atoms and alkyl having 1 to 4 carbon atoms which is monosubstituted by nitro, cyano, isocyanato, fluorine, chlorine, bromine, iodine, hydroxyl, alkoxy having 1 to 3 carbon atoms, mercapto, alkylthio having 1 to 3 carbon atoms, alkylcarbonyl and alkylcarbonyloxy having 1 to 3 carbon atoms in the alkyl part, and alkoxycarbonyl having 1 to 3 carbon atoms in the alkoxy part; alkinyl having 3 to 6 carbon atoms; alkinyl which has 3 or 4 carbon atoms in the alkinyl part and is monosubstituted by fluorine, chlorine, bromine, iodine, alkoxy or alkylthio, each having 1 to 3 carbon atoms, alkylcarbonyl and alkylcarbonyloxy, each having 1 to 3 carbon atoms per alkyl part; cyclohexyl, cyclopentenyl, cyclohexenyl, cycloheptenyl and cyclopentyl which is optionally monosubstituted to trisubstituted by methyl or ethyl; benzyl, phenylethyl, naphthyl, naphthylethyl, naphthylmethyl and phenyl which is optionally monosubstituted to trisubstituted by identical or different substituents from amongst fluorine, chlorine, bromine, iodine, nitro, cyano, isocyanato, phenyl, methyl, ethyl, n- and iso-propyl, tert.-butyl, mercapto, methoxy, ethoxy, propoxy, methoxycarbonyl, ethoxycarbonyl, methylcarbonyl, ethylcarbonyl, propylcarbonyl, trichloromethyl, fluorodichloromethyl, trichloroethyl, trichloromethoxy and trichloroethoxy; or furyl, pyrrolyl, imidazolyl, piperazinyl, isoxazolyl, morpholinyl, 1,5-dioxaspiroundecanyl or 1,3-dioxa-cyclohexyl which is optionally monosubstituted to trisubstituted by fluorine, chlorine, methyl, ethyl or propyl; and $R^2$ represents alkyl having 1 to 5 carbon atoms; alkyl and alkenyl, each of which has up to 6 carbon atoms per radical and is monosubstituted by fluorine, chlorine, bromine, cyano or alkoxy having 1 to 3 carbon atoms; cycloalkyl and cycloalkenyl, each of which has 4 to 7 carbon atoms and is optionally substituted by alkyl having 1 to 3 carbon atoms; or fluorenyl or benzyl which is optionally monosubstituted to trisubstituted in the aryl part by phenyl, fluorine, chlorine, bromine, nitro and alkyl and alkoxy, each having 1 to 3 carbon atoms.

3. A compound according to claim 1, wherein such compound is 3-methyl-6-phenylthio-2-thioxo-1,3,5-thiadiazin-4-one of the formula

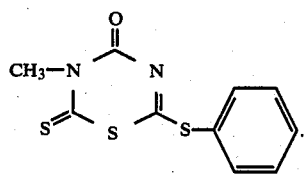

4. A compound according to claim 1, wherein such compound is 6-(1-carboethoxy-ethoxy)-3-methyl-2-thioxo-1,3,5-thiadiazin-4-one of the formula

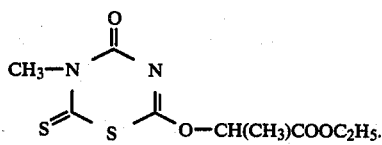

5. A compound according to claim 1, wherein such compound is 3-ethyl-6-phenylthio-2-thioxo-1,3,5-thiadiazin-4-one of the formula

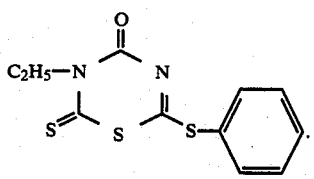

6. A compound according to claim 1, wherein such compound is 6-(4-methoxyphenylthio)-3-methyl-2-thioxo-1,3,5-thiadiazin-4-one of the formula

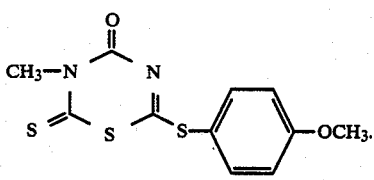

7. A compound according to claim 1, wherein such compound is 3-methyl-6-propargyloxy-2-thioxo-1,3,5-thiadiazin-4-one of the formula

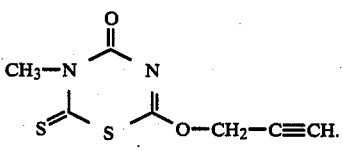

8. A fungicidal composition comprising a fungicidally effective amount of a compound according to claim 1 in admixture with a diluent.

9. A method of combating fungi which comprises administering to such fungi or to a fungus habitat a fungicidally effective amount of a compound according to claim 1.

10. The method according to claim 9, wherein such compound is 3-methyl-6-phenylthio-2-thioxo-1,3,5-thiadiazin-4-one, 6-(1-carboethoxy-ethoxy)-3-methyl-2-thioxo-1,3,5-thiadiazin-4-one, 3-ethyl-6-phenylthio-2-thioxo-1,3,5-thiadiazin-4-one, 6-(4-methoxyphenylthio)-3-methyl-2-thioxo-1,3,5-thiadiazin-4-one or 3-methyl-6-propargyloxy-2-thioxo-1,3,5-thiadiazin-4-one.

* * * * *